US011629144B2

(12) United States Patent
Zhu et al.

(10) Patent No.: US 11,629,144 B2
(45) Date of Patent: Apr. 18, 2023

(54) CRYSTAL FORM OF MONOMETHANESULFONATE OF DEUTERATED 3-(4,5-SUBSTITUTED AMINOPYRIMIDINE)PHENYL COMPOUND AND PREPARATION METHOD THEREFOR

(71) Applicant: NANJING CHUANGTE PHARMACEUTICAL TECHNOLOGY CO., LTD., Jiangsu (CN)

(72) Inventors: Yongqiang Zhu, Jiangsu (CN); Yang Yang, Jiangsu (CN); Ou Hai, Jiangsu (CN); Zhaogang Liu, Jiangsu (CN); Chao Feng, Jiangsu (CN)

(73) Assignee: NANJING CHUANGTE PHARMACEUTICAL TECHNOLOGY CO., LTD, Jiangsu (CN)

( * ) Notice: Subject to any disclaimer, the term of this patent is extended or adjusted under 35 U.S.C. 154(b) by 178 days.

(21) Appl. No.: 16/980,596

(22) PCT Filed: Mar. 15, 2019

(86) PCT No.: PCT/CN2019/078200
§ 371 (c)(1),
(2) Date: Sep. 14, 2020

(87) PCT Pub. No.: WO2019/174623
PCT Pub. Date: Sep. 19, 2019

(65) Prior Publication Data
US 2021/0053971 A1    Feb. 25, 2021

(30) Foreign Application Priority Data
Mar. 16, 2018   (CN) .......................... 201810220003.4

(51) Int. Cl.
*C07D 471/06* (2006.01)
*C07C 309/04* (2006.01)

(52) U.S. Cl.
CPC .......... *C07D 471/06* (2013.01); *C07C 309/04* (2013.01); *C07B 2200/13* (2013.01)

(58) Field of Classification Search
None
See application file for complete search history.

(56) References Cited

U.S. PATENT DOCUMENTS 10,654,851 B2 *  5/2020  Zhu ......................... A61P 35/00

FOREIGN PATENT DOCUMENTS

| CN | 107344934 A | 11/2017 |
| CN | 107840847 A | 3/2018 |
| WO | WO 2016/054987 A1 | 4/2016 |
| WO | WO 2019/174623 A1 | 9/2019 |

OTHER PUBLICATIONS

Seshacharyulu et al., Targeting the EGFR signaling pathway in cancer therapy. Expert Opinion on Therapeutic Targets, 2012, 16, 15-31.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
International Preliminary Report on Patentability dated Sep. 22, 2020, including Written Opinion of the International Searching Authority dated May 17, 2019, in connection with PCT International Application No. PCT/CN2019/078200.
International Search Report dated May 17, 2019 in connection with PCT International Application No. PCT/CN2019/078200.
Written Opinion (form PCT/ISA/237) dated May 17, 2019 in connection with PCT International Application No. PCT/CN2019/078200.

* cited by examiner

*Primary Examiner* — Po-Chih Chen

(57) ABSTRACT

Disclosed in the present invention are a crystal form of monomethanesulfonate of a deuterated 3-(4,5-substituted aminopyrimidine)phenyl compound as represented by formula I, and a preparation method therefor. The crystal form is highly stable, can be used for treatment or prevention of diseases or conditions by means of epidermal growth factor receptors (EGFRs) in some mutation forms, can effectively inhibit the growth of a variety of tumor cells, and have an inhibiting effect on other proteases of EGFR and Her families, and thus can be used for preparing antitumor drugs.

18 Claims, 10 Drawing Sheets

CRYSTAL FORM OF MONOMETHANESULFONATE OF DEUTERATED 3-(4,5-SUBSTITUTED AMINOPYRIMIDINE)PHENYL COMPOUND AND PREPARATION METHOD THEREFOR

RELATED APPLICATIONS

This application is a § 371 national stage of PCT International Application No. PCT/CN2019/078200, filed on Mar. 15, 2019, designating the United States and claiming priority of Chinese Application Nos. Nos. 201810220003.4, filed Mar. 16, 2018.

BACKGROUND

Technical Field

The present invention belongs to the field of pharmacy, and in particular, relates to a crystal form of monomethanesulfonate of a compound N-(5-((4-(5,6-dihydro-4H-pyrrolo[3,2,1-ij]quinoline-1-yl)amino)-4-methoxy-2-(methyl(2-(methyl-$d_3$)amino)ethyl)amino)phenyl)acetamide and a preparation method therefor.

Related Art

The structural formula of the compound N-(5-((4-(5,6-dihydro-4H-pyrrolo[3,2,1-ij]quinoline-1-yl)amino)-4-methoxy-2-(methyl(2-(methyl-$d_3$)amino)ethyl)amino)phenyl)acetamide represented by formula I is:

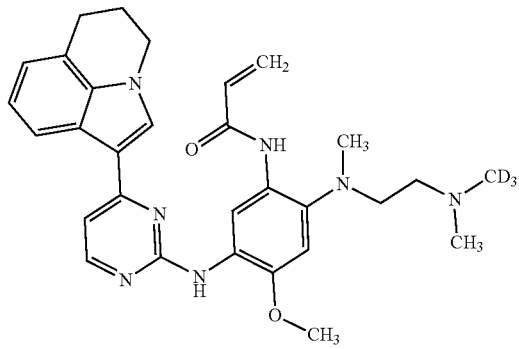

I

The compound as shown in formula I is an EGFR (epidermal growth factor receptor) tuner in pharmacy. An active pharmaceutical ingredient prepared from the monomethanesulfonate of the compound as shown in formula I ingredient can be used for the prevention and treatment of diseases mediated by certain epidermal growth factor receptors with variant forms. Different crystal forms of the same compound may cause different physicochemical properties, for example, different solubilities, thermodynamic stability, and densities or melting points of different forms. Such physicochemical properties may have an important effect on the efficacy or bioavailability of the active ingredient, and thus it is of great significance to obtain a stable crystal form of a compound.

SUMMARY

The present invention mainly provides a crystal form of monomethanesulfonate of a deuterated 3-(4,5-substituted aminopyrimidine)phenyl compound as represented by formula I and a preparation method therefor, specifically as follows:

A crystal form A of monomethanesulfonate of a deuterated 3-(4,5-substituted aminopyrimidine)phenyl compound as represented by formula I:

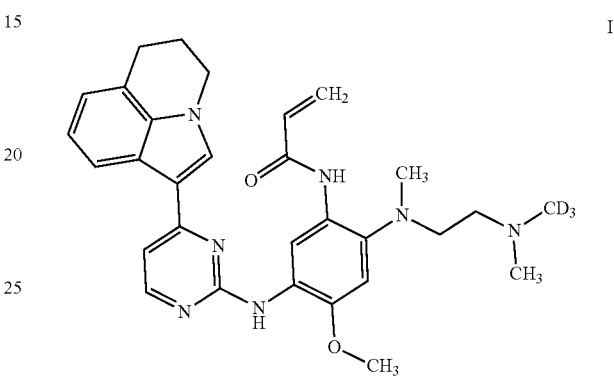

I

In X-ray powder diffraction of the crystal form A, a 2θ diffraction angle has characteristic peaks at 15.42±0.2°, 17.86±0.2°, 20.58±0.2°, 21.58±0.2°, 23.86±0.2°, and 24.96±0.2°; furthermore, the 2θ diffraction angle also has characteristic peaks at 6.34±0.2°, 10.24±0.2°, 10.72±0.2°, 14.94±0.2°, 15.42±0.2°, 16.88±0.2°, 17.86±0.2°, 20.58±0.2°, 21.58±0.2°, 23.86±0.2°, 24.96±0.2°, 26.28±0.2°, and 27.58±0.2°.

Further, the crystal form A has an X-ray powder diffraction pattern basically as shown in FIG. 1.

Further, the crystal form A has a thermogravimetric analysis graph basically as shown in FIG. 3 and a differential scanning calorimetry curve basically as shown in FIG. 4.

Further, the crystal form A has infrared spectra with the following characteristic absorption peaks: 3249 cm$^{-1}$, 3019 cm$^{-1}$, 1942 cm$^{-1}$, 1906 cm$^{-1}$, 1672 cm$^{-1}$, 1575 cm$^{-1}$, 1552 cm$^{-1}$, 1411 cm$^{-1}$, 1368 cm$^{-1}$, 727 cm$^{-1}$, 558 cm$^{-1}$, and 522 cm$^{-1}$.

The preparation method of the crystal form A is as follows: at the temperature of 30-50° C., dissolving a compound as shown in formula I in dichloromethane, and dropwise adding methanesulfonic acid; stirring and crystallizing at the temperature of 0-30° C.; filtering and drying to obtain the crystal form A; where the use amount of the dichloromethane is 5-40 times that of the compound shown in formula I in ml/g unit; and further, the use amount of the dichloromethane is 10-20 times that of the compound shown in formula I in ml/g unit; and the molar ratio of the methanesulfonic acid to the compound shown in formula I is (0.1-1):1.

A crystal form B of monomethanesulfonate of the deuterated 3-(4,5-substituted aminopyrimidine)phenyl compound as represented by formula I:

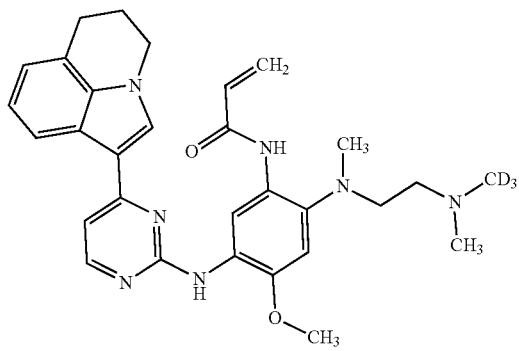

In X-ray powder diffraction of the crystal form B, a 2θ diffraction angle has characteristic peaks at 10.38±0.2°, 14.9±0.2°, 18.1±0.2°, 22.68±0.2°, and 26.20±0.2°; and further, the 2θ diffraction angle also has characteristic peaks at 7.20±0.2°, 8.00±0.2°, 8.50±0.2°, 10.38±0.2°, 14.9±0.2°, 16.06±0.2°, 18.1±0.2°, 19.28±0.2°, 20.88±0.2°, 21.96±0.2°, 22.68±0.2°, 23.54±0.2°, and 26.20±0.2°.

Further, the crystal form B has an X-ray powder diffraction pattern basically as shown in FIG. 5.

Further, the crystal form B has a thermogravimetric analysis graph basically as shown in FIG. 7 and a differential scanning calorimetry curve basically as shown in FIG. 8.

Further, the crystal form B has infrared spectra with the following characteristic absorption peaks: 3248 cm$^{-1}$, 3103 cm$^{-1}$, 1906 cm$^{-1}$, 1671 cm$^{-1}$, 1618 cm$^{-1}$, 1575 cm$^{-1}$, 1533 cm$^{-1}$, 1141 cm$^{-1}$, 1235 cm$^{-1}$, 1162 cm$^{-1}$ and 807 cm$^{-1}$.

A preparation method of the crystal B includes the following steps:
1) mixing the compound shown in formula I with a solvent at the temperature of 50-80° C., and dropwise adding methanesulfonic acid;
2) stirring and crystallizing at the temperature of 0-30° C.; and
3) filtering and drying to obtain the crystal form B.

The solvent is selected from acetonitrile, acetone or a mixture of the acetonitrile and the acetone, and the use amount of the solvent is 5-40 times that of the compound shown in formula I in ml/g unit; and further, the use amount of the solvent is 10-20 times that of the compound shown in formula I in ml/g unit.

The molar ratio of the methanesulfonic acid to the compound as shown in formula I is (0.1-1):1.

The present invention also discloses application of the crystal forms A and B of the monomethanesulfonate of the compound shown in formula I in drugs for the treatment or prevention of tumors, where the tumors are selected from non-small cell lung cancer, small cell lung cancer, pancreatic cancer, breast cancer, prostate cancer, liver cancer, skin cancer, epithelial cell carcinoma, gastrointestinal stromal tumor, leukemia, histiocytic lymphoma, and nasopharyngeal carcinoma.

The crystal forms A and B of the monomethanesulfonate of the compound shown in formula I disclosed in the present invention are used for the treatment or prevention of diseases, obstacles, disorders, or conditions medicated by EGFR or EGFR in the form of an activated mutant or a resistant mutant; the diseases, obstacles, disorders, or conditions medicated by EGFR or EGFR in the form of the activated mutant or the resistant mutant are selected from the non-small cell lung cancer, the small cell lung cancer, the pancreatic cancer, the breast cancer, the prostate cancer, the liver cancer, the skin cancer, the epithelial cell carcinoma, the gastrointestinal stromal tumor, the leukemia, the histiocytic lymphoma, or the nasopharyngeal cancer; and EGFR in the form of the activated mutant or resistant mutant is selected from an L858R activated mutant, an Exon19 deletion activated mutant, and a T790M resistant mutant.

The crystal forms A and B of the monomethanesulfonate of the compound shown in formula I of the present invention can be combined with other known drugs for the treatment or improvement of similar conditions. During combined administration, the administration mode and dosage of the original drug are kept unchanged, and the crystal form A or B of the monomethanesulfonate of the compound shown in formula I is orally taken simultaneously or subsequently. When the crystal form A or B of the monomethanesulfonate of the compound shown in formula I and one or more other drugs are orally taken at the same time, a pharmaceutical composition containing one or more known drugs and the crystal form B of the monomethanesulfonate of the compound shown in formula I at the same time is preferably used. Drug combination also includes orally taking the crystal form A or B of the monomethanesulfonate of the compound as shown in formula I and one or more other known drugs in overlapping periods of time. When the crystal form A or B of the monomethanesulfonate of the compound shown in formula I is combined with one or more other drugs, the dosage of the crystal form A or B of the monomethanesulfonate of the compound shown in formula I or the known drugs can be lower than the dosage of the crystal form A or B of the monomethanesulfonate of the compound or the known drugs when used alone. Pharmaceuticals or active ingredients which can be used in pharmaceutical combination with the crystal form A or B of the monomethanesulfonate of the compound as shown in formula I include, but are not limited to, the following substances:

an estrogen receptor regulator, an androgen receptor regulator, a retinal receptor regulator, a cytotoxin/cell inhibitor, an anti-proliferation agent, a protein transferase inhibitor, an HMG-CoA reductase inhibitor, an HIV protein kinase inhibitor, a reverse transcriptase inhibitor, an angiogenesis inhibitor, a cell proliferation and survival signal inhibitor, drugs and apoptosis inducers disturbing cell cycle checkpoint, cytotoxic drugs, a tyrosine protein inhibitor, an EGFR inhibitor, a VEGFR inhibitor, a serine/threonine protein inhibitor, a Bcr-Abl inhibitor, a c-Kit inhibitor, a Met inhibitor, a Raf inhibitor, an MEK inhibitor, an MMP inhibitor, a topoisomerase inhibitor, a histidine deacetylase inhibitor, a proteasome inhibitor, a CDK inhibitor, a Bcl-2 family protein inhibitor, an MDM2 family protein inhibitor, an IAP family protein inhibitor, an STAT family protein inhibitor, a PI3K inhibitor, an ATK inhibitor, an integrin blocker, interferon, interleukin-12, a COX-2 inhibitor, P53, a P53 activator, a VEGF antibody, an EGF antibody, and the like.

Further, pharmaceuticals or active ingredients which can be used in pharmaceutical combination with the crystal form A or B of the monomethanesulfonate of the compound as shown in formula I include, but are not limited to, the following substances: aldesleukin, alendronic acid, interferon, alitretinoin, allopurinol, sodium allopurinol, palonosetron hydrochloride, altretamine, aminoglutethimide, amifostine, amrubicin, amsacrine, anastrozole, dolasetron, aranesp, arglabin, arsenic trioxide, aromasin, 5-azacytidine, azathioprine, bcg vaccine or tice bcg vaccine, bestatin, betamethasone acetate, a betamethasone sodium phosphate inhibitor, bexarotene, bleomycin sulphate, bromouridine, bortezomib, carfilzomib, busulfan, calcitonin, alemtuzumab injection, capecitabine, carboplatin, casodex, cefesone, celmoleukin, daunorubicin, chlorambucil, cisplatin, cladribine, clodronic acid, cyclophosphamide, cytosine arabinoside, dacarbazine, actinomycin D, liposomal daunorubicin, dexamethasone, dexamethasone phosphate, estradiol valerate, denileukindiftitox 2, Depo-Medrol, deslorelin, dexrazoxane, diethylstilbestrol, fluconazole, docetaxel, doxifluridine, adriamycin, dronabinol, Cho-166-chitosan complex, eligrand, rasburicase, epirubicin hydrochloride, aprepitant, epirubicin, epoetin alfa, erythrogenin, eptaplatin, levamisole tablets, an oestradiol inhibitor, 17-lyase estradiol, estramustine sodium phosphate, ethinyloestradiol, amifostine, etidronic acid, etopophos, etoposide, fadrozole, a nolvadex preparation, filgrastim, finasteride, fegrastim, floxuridine, fluconazole, fludarabine, 5-fluorodeoxyuridine monophosphate, 5-fluorouracil, fluoxymesterone, flutamide, formestane, I-pyrimidine, arabinofuranosylcytosine-5 furan hard acyl phosphate, fotemustine, fulvestrant, gamma globulin, gemcitabine, gemtuzumabozogamicin, imatinibmesylate, carmustine wafer capsules, goserelin, lucanthone hydrochloride, histrelin, topotecan hydrochloride for injection, hydrocortisone, erythro-hydroxynonyl adenine, hydroxycarbamide, ibritumomabtiuxetan, idarubicin, ifosfamide, interleukin-2, intron A, gefitinib, irinotecan, granisetron hydrochloride injection, lentinan sulfate, letrozole, leucovorin, leuprorelin, leuprorelin acetate, levo-tetramisole, calcium levofolinate, levothyroxine sodium, a levothyroxine sodium preparation, lumostine, lonidamine, dronabinol, nitrogen mustard, mecobalamine, medroxyprogesterone acetate, megestrol acetate, melphalan, esterified estrogens, 6-mercaptopurine, mesna, amethopterin, methyl aminolevulinate, miltefosine, minocycline, mitomycin C, mitotane, mitoxantrone, trilostane, adriamycin citrate liposomes, nedaplatin, pegfilgrastim, oprelvekin, neupogen, nilutamide, tamoxifen, NSC-631570, recombinant human interleukin l-group, octreotide, ondansetron hydrochloride, dehydrocortisone oral solution, oxaliplatin, paclitaxel, prednisone sodium phosphate preparation, pegaspargase, pegasys, pentostatin, picibanil, pilocarpine hydrochloride, pirarubicin, plicamycin, porfimer sodium, prednimustine, prednisolone steaglate, prednisone, premarin, procarbazine, recombinant human erythropoietin, raltitrexed, recombinant human interferon beta 1a solution for injection, rhenium etidronate-186, rituximab, rdoxon, romurtide, pilocarpine hydrochloride tablets, octreotide, sargramostim, semustine, sizofiran, sobuzoxane, methylprednisolone sodium succinate, spar-fosic acid, stem cell treatment, streptozocin, strontium chloride-89, levothyroxine sodium, tamoxifen, tamsulosin, tasonermin, tastolactone, docetaxel, teceleukin, temozolomide, teniposide, testosterone propionate, thioguanine, thiotepa, thyrotropic hormone, tiludronate, topotecan, toremifene, tositumomab, trastuzumab, treosulfan, tretinoin, methotrexate tablets, trimethylamine, trimetrexate, triptorelin acetate, triptorelinpamoate, UFT, uridine, valrubicin, vesnarinone, vinblastine, vincristine, vindesine, navelbine, virulizin, dexrazoxane, zinostatinstimalamer, ondansetron, a paclitaxel protein stable preparation, acolbifene, affinitak, aminopterin, arzoxifene, asoprisnil, atamestane, BAY43-9006, avastin, CCI-779, CDC-501, celebrex, cetuximab, crisnatol, cyproterone acetate, decitabine, DN-101/doxorubicin-MTC, dSLIM, dutasteride, edotecarin, eflomithine, irinotecan, fenretinide, histamine dihydrochloride, histrelin hydrogel implants, holmium-166 DOTMP, ibandronic acid, ixabepilone, keyhole limpet hemocyanin, L-651582, lanreotide, lasofoxifene, libra, lonafamib, miproxifene, minodronate, MS-209, liposomal MEP-PE, MX-6, nafarelin, nemorubicin, simvastatin, nolatrexed, oblimersen, onco-TCS, osidem, paclitaxel polyglutamate, pamidronate disodium injection, PN-401, OS-21, quazepam, R-1549, raloxifene, onconase, 13-cis-retinoic acid, satraplatin, scocalcitol, T-138067, tarceva, docosahexacnoic acid paclitaxel, thymosina, tiazofurine, tipifarnib, tirapazamine, TLK-286, toremifene, trans MID-lo7R, valspodar, vapreotide, vatalanob, verteporfin, vinflunine, Z-100, zoledronic acid or a combination thereof.

The present invention also provides a pharmaceutical composition, and the pharmaceutical composition includes the crystal forms A and B of the monomethanesulfonate of the compound shown in formula I or pharmaceutically acceptable salts thereof and pharmaceutically acceptable auxiliary materials or carriers.

The crystal form A or B of the monomethanesulfonate of the compound shown in formula I disclosed herein may be further processed into any type of pharmaceutical preparations or dosage form well known to those skilled in the art; solid form compositions include powder, tablets, capsules, pills, pulvis, and suspensions; and liquid form preparations include solutions, suspensions, and emulsions. The pharmaceutical composition may be composed of the crystal form B of the monomethanesulfonate of the compound shown in formula I, one or more non-toxic pharmaceutically acceptable auxiliary materials or carriers, and other active ingredients if necessary. As used herein, the phrase "pharmaceutically acceptable auxiliary materials or carriers" refers to pharmaceutically acceptable materials, ingredients or media, such as liquid or solid fillers, diluents, auxiliary materials, solvents, or encapsulating materials, including carrying or transporting a major pharmaceutically reagent from one organ or a certain portion of the body to another organ or another certain portion of the body. Each carrier must be "acceptable" and can be compatible with other forms of pharmaceutical ingredients without causing harm to a patient. Some examples of pharmaceutically acceptable carriers include sugars, such as lactose, glucose, and sucrose; starches, such as wheat starch and potato starch; cellulose and derivatives thereof, such as sodium carboxymethyl cellulose, ethyl cellulose, cellulose acetate, powdered tragacanth, malt, gelatin, and talcum powder; auxiliary materials, such as cocoa butter and suppository waxes; oils, such as peanut oil, cottonseed oil, safflower oil, sesame oil, olive oil, corn oil, and soybean oil; glycols, such as butanediol; polyols, such as glycerol, sorbitol, mannitol, and polyethylene glycol; esters, such as ethyl oleate and ethyl laurate; agar; buffering agents, such as magnesium hydroxide and aluminum hydroxide; alginic acid pyrogen-free water; physiological saline; Ringer's solution; ethanol; phosphate buffering solution; and other non-toxic compatible substances for use in pharmaceutical preparations.

When the crystal forms of the monomethanesulfonate of the compound shown in formula I of the present invention are medicaments for the treatment in humans and animals, they may be administered alone or as pharmaceutical compositions. For example, the crystal form of the monomethanesulfonate of the compound includes 0.1%-99.5% (preferably, 0.5%-90%) of an active ingredient and a pharmaceutically acceptable carrier.

The present invention also provides a pharmaceutical package or kit including one or more packages containing a pharmaceutical combination of one or more of the ingredients of the present invention. Optionally, the production of such packages is regulated announcements of government institutions, and pharmaceutical or biological products and treatment formulations to humans are used or sold with the disclosed methods permitted in the production regulations.

Researches show that the X-ray diffraction pattern of a sample of the crystal form A of the monomethanesulfonate of the compound shown in formula I is measured under high-temperature, high-humidity, and illumination conditions for 15 days, and the result shows that the crystal form A of the monomethanesulfonate can be converted into the crystal form B of the monomethanesulfonate under the high-temperature or high-humidity condition, which indicates that the crystal form A of the monomethanesulfonate is easy to generate a crystal transformation phenomenon under the high-temperature or high-humidity condition.

The crystal form B of the monomethanesulfonate of the compound as shown in formula I involved in the present invention has beneficial physical properties for pharmaceutical processing and application, including high stability and non-hygroscopicity. Firstly, a single DSC peak value of the crystal form B is observed, proving that the crystal form B has a stable heat exchange range, and crystals are stable per se; and secondly, in an accelerated lofting test (the temperature is 40±2° C., and the relative humidity is 75%±5%) and a long-term lofting test (the temperature is 25±5° C., and the relative humidity is 60%±10%), the appearance, the purity, the related impurities, and the content of the crystal form B are not greatly changed, proving the good stability of the crystal form B under the condition.

The solvent adopted in the preparation process of the crystal forms of the monomethanesulfonate of the compound shown in formula I provided by the present invention has low toxicity, the preparation process is safe, and the product obtained has relatively high purity.

DETAILED DESCRIPTION

Figure 1:
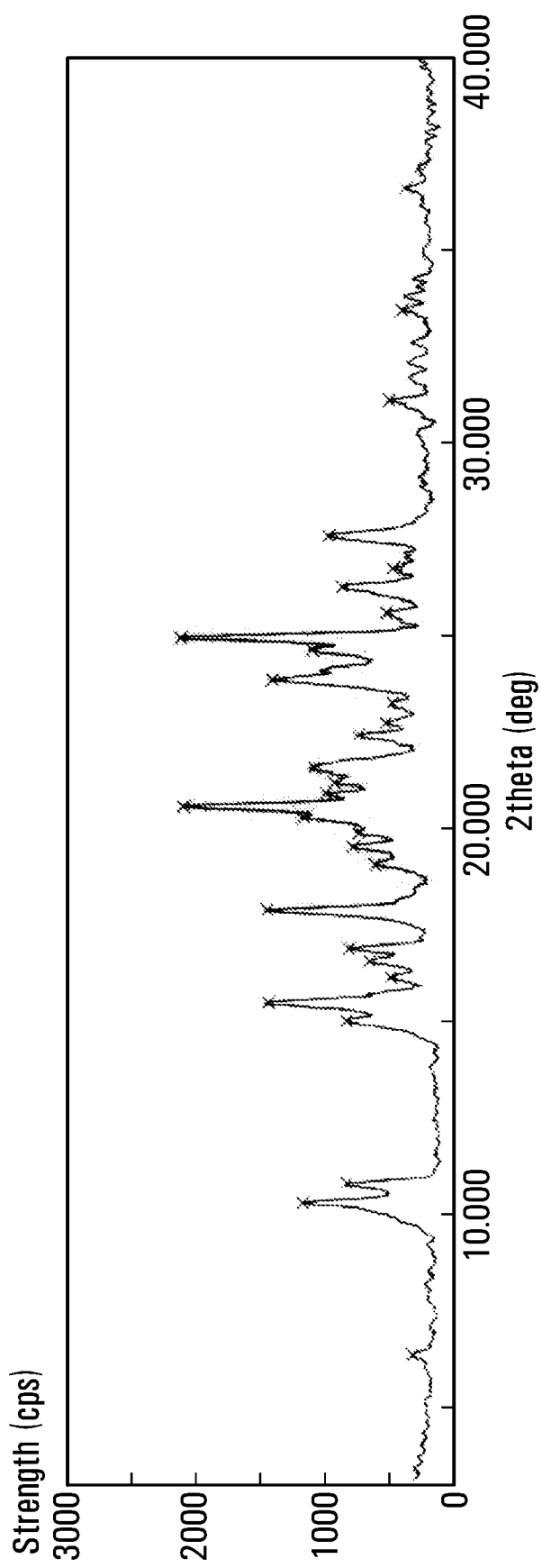
FIG. 1 is an X-ray powder diffraction pattern of a crystal form A of monomethanesulfonate of a compound shown in formula I in an embodiment 2.
Figure 2:
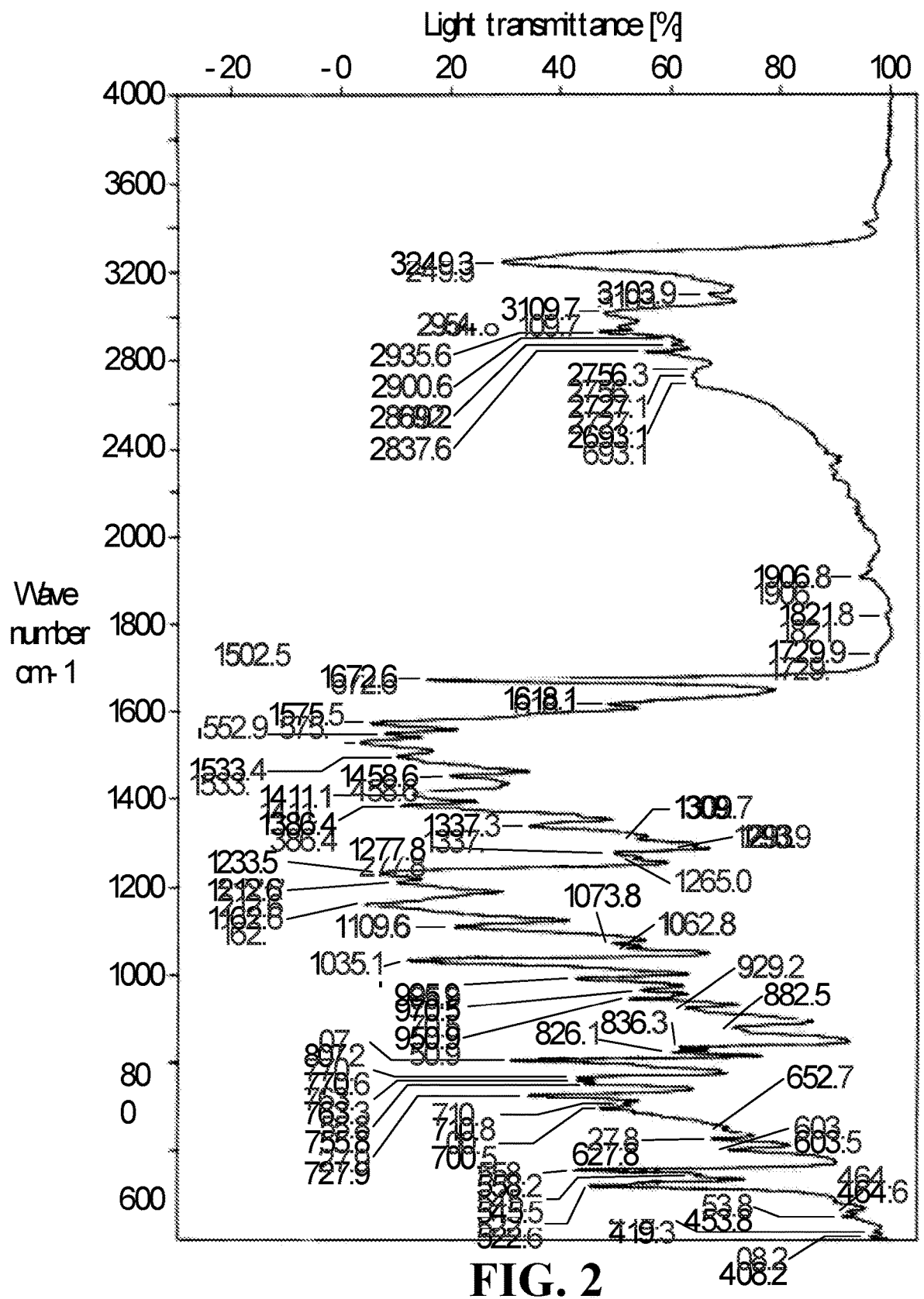
FIG. 2 is an infrared spectrogram of the crystal form A of the monomethanesulfonate of the compound shown in formula I in the embodiment 2.

The following detailed embodiments describe how to prepare the various compounds and/or perform the various methods of the present invention, and are to be understood as merely illustrative, and not restrictive, of the above disclosure. One skilled in the art will be able to quickly and accurately identify the reactants and variations in reaction conditions and techniques.

Embodiment 1: Preparation of a Compound in Formula I

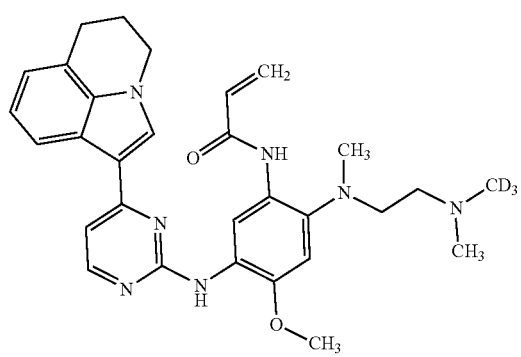

A synthetic mute is as follows:

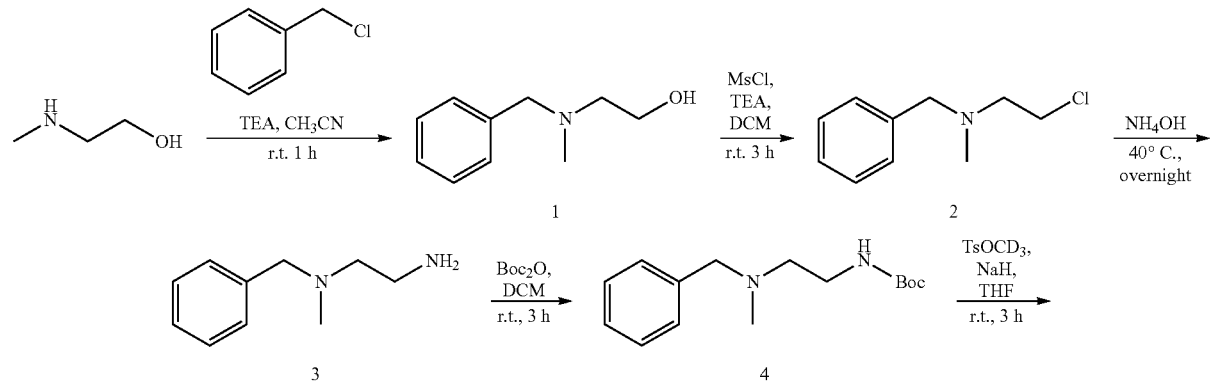

-continued
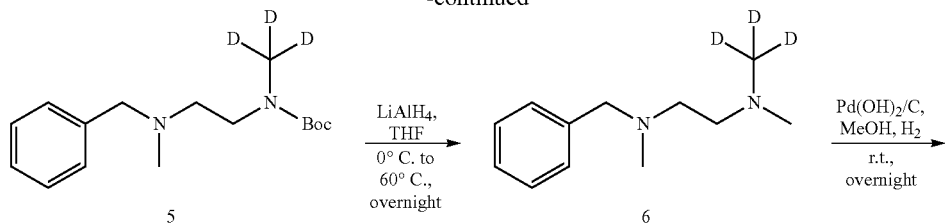
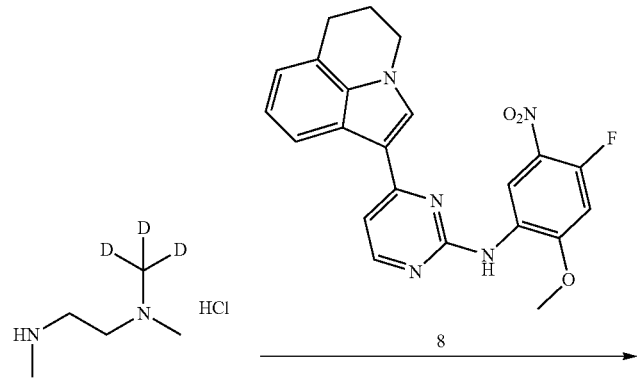
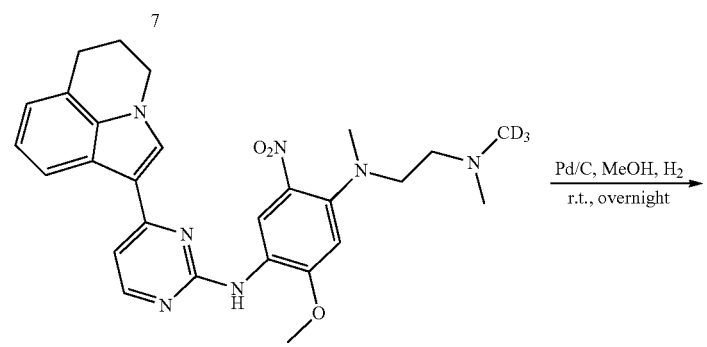
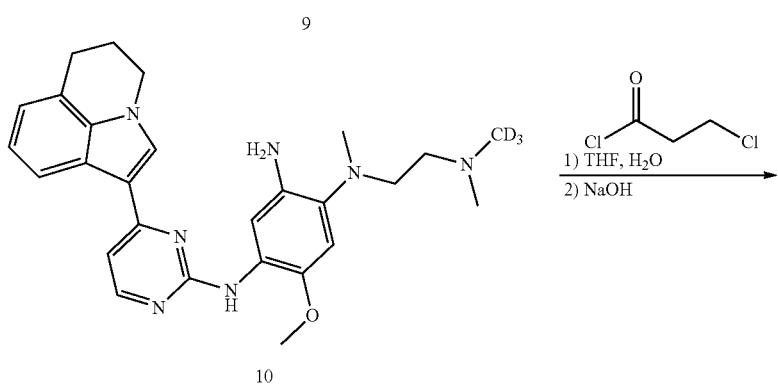
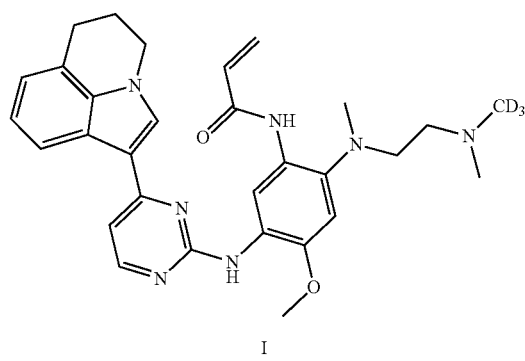

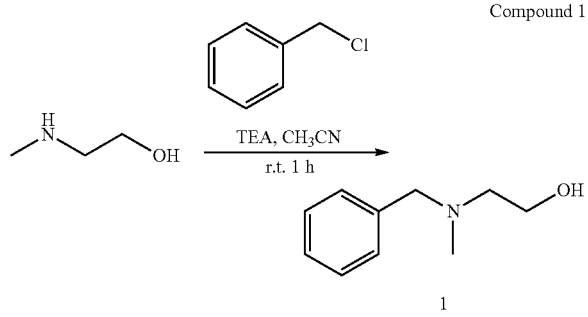

A 250 mL single-neck flask was taken, N-methylethanolamine (10 g, 133.1 mmol), TEA (26.9 g, 266.3 mmol) and acetonitrile (100 mL) were added into the single-neck flask separately, then benzyl chloride (23.9 g, 139.8 mmol) was slowly added dropwise to a reaction solution at 0° C., the mixture was kept stirring for 1 h at room temperature, no raw material remaining was monitored by TLC, a solvent was distilled off under reduced pressure, and the mixture was purified by column chromatography to obtain 21 g of colorless liquid which is the compound 1 with the yield of 95.5%.

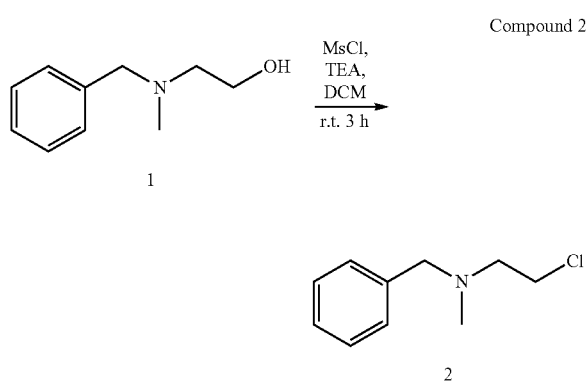

A 250 mL eggplant-shaped flask was taken, the compound 1 (21 g, 127.1 mmol), TEA (25.7 g, 254.2 mmol) and DCM (100 ml) were added into the eggplant-shaped flask, and then MsCl (14.6 g, 127.1 mmol) was dropwise added at 0° C. A reaction solution was stirred at room temperature for 3 h, no raw material remaining was monitored by TLC, a solvent was distilled off under reduced pressure, and the mixture was purified by column chromatography to obtain 20 g of faint yellow liquid which is the compound 2 with the yield of 85.6%.

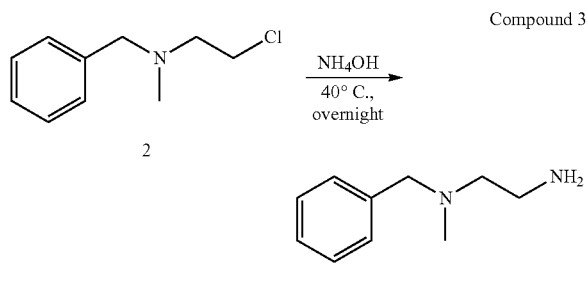

A 500 mL sealed tube was taken, the compound 2 (20 g, 108.9 mmol) and 215 mL of ammonia water were added in the sealed tube, mixed liquid was stirred overnight at 40° C., no raw material remaining was monitored by TLC, and the mixed liquid was purified by column chromatography to obtain 15 g of colorless liquid which is the compound 3 with the yield of 84%.

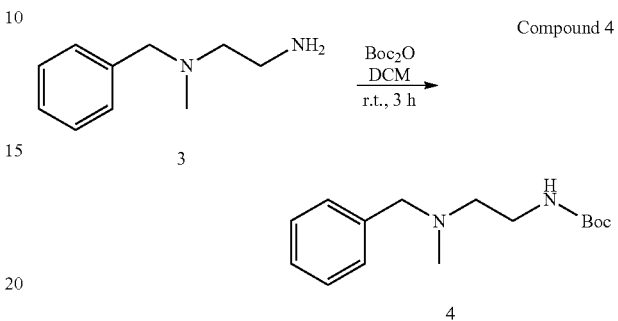

A 500 mL eggplant-shaped flask was taken, the compound 3 (15 g, 91.3 mmol) and DCM (200 mL) were added in the eggplant-shaped flask, Boc$_2$O (19.9 g, 91.3 mmol) was slowly dropwise added at room temperature, the mixture was kept stirring for 3 h at room temperature after completion of the addition, no raw material remaining was monitored by TLC, a solvent was distilled off under reduced pressure, and the mixture was purified by column chromatography to obtain 21 g of the compound 4 which is white solid and has the yield of 87%.

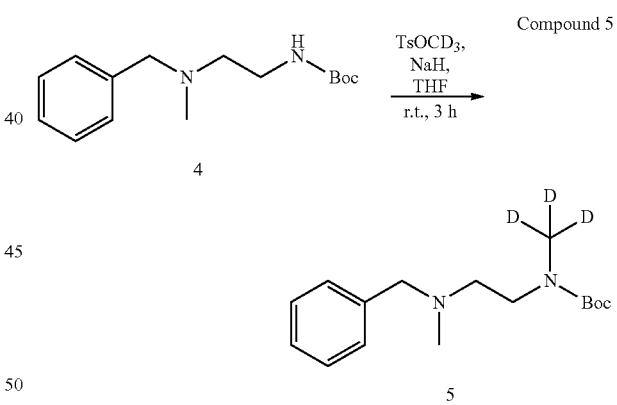

A 100 mL eggplant-shaped flask was taken, the compound 4 (10 g, 37.8 mmol) and DMF (40 mL) were added to the eggplant-shaped flask, NaH (2.3 g, 56.7 mmol) was added in batches, the mixture was stirred for 30 min, was added with a DMF (10 mL) solution of TsOCD$_3$ (7.9 g, 41.6 mmol), and then was stirred at room temperature for 3 h, no raw material remaining was monitored by TLC, the mixture was quenched by addition of 150 mL of H$_2$O, and was extracted by addition of EA (50 mL*3), organic phases were combined, the mixture was washed with brine, and was dried through anhydrous Na$_2$SO$_4$, a solvent was distilled off under reduced pressure, and the mixture was purified by column chromatography to obtain 8.5 g of the compound 5 as a white solid with the yield of 80%.

Compound 6

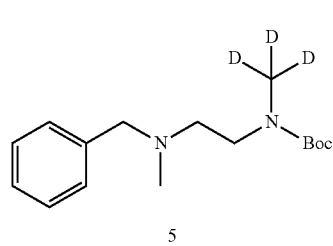

5

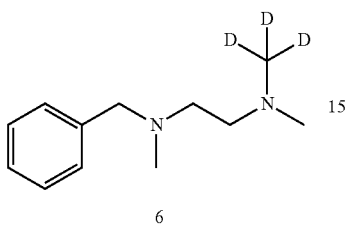

6

A 250 mL eggplant-shaped flask was taken, the compound 5 (8.5 g, 30.18 mmol) and THF (80 mL) were added into the eggplant-shaped flask, LiAlH$_4$ (3.4 g, 90.59 mmol) was added in batches under ice bath, then the mixture was heated to 60° C. overnight, no raw material remaining was monitored by TLC, the mixture was quenched by slow addition of Na$_2$SO$_4$·10H$_2$O, solid was removed by filtration, the filtrate was collected, a solvent was distilled off under reduced pressure, and the mixture was purified by column chromatography to obtain 4.5 g of colorless liquid which is the compound 6 and has the yield of 76.3%.

Compound 7

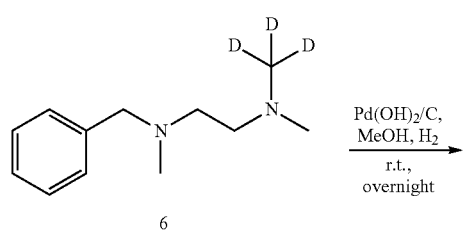

6

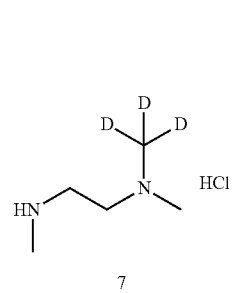

7

A 100 mL eggplant-shaped flask was taken, the compound 6 (4.5 g, 23 mmol), MeOH (50 mL) and Pd(OH)$_2$/C (200 mg) were added into the eggplant-shaped flask respectively, hydrogen was changed for 3 times by vacuum pumping, the mixture was stirred at room temperature overnight, no raw material remaining was monitored by TLC, Pd(OH)$_2$/C was removed by filtration, the pH value of a reaction solution was regulated to acidity, and a solvent was distilled off under reduced pressure to obtain 2.8 g of white solid which is the compound 7 with the yield of 85.9%.

Compound 8

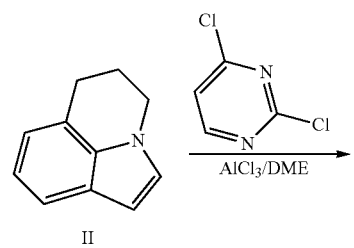

II

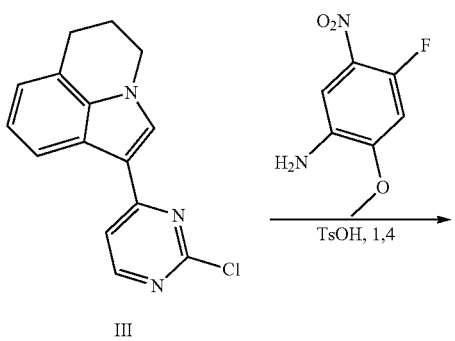

III

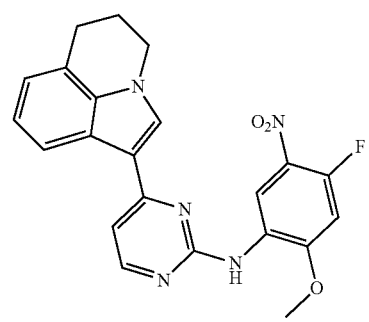

8

A 250 mL eggplant-shaped flask was taken, 2,4-dichloropyrimidine (11.37 g, 76.33 mmol), aluminum trichloride (10.18 g, 76.33 mmol) and 100 mL of ethylene glycol dimethyl ether (DME) were added into the eggplant-shaped flask respectively, and the mixture was stirred at room temperature for 20 minutes. Then a compound II (10.00 g, 63.61 mmol) was added in batches, the temperature rises to 80° C. and reaction was carried out for 6 h. The reaction was stopped and the mixture was cooled to room temperature, 100 mL of water was added, the mixture was stirred for 2 h and was filtered, and solid was washed by ethanol and dried under vacuum to obtain 15.46 g of a red crude product which is a compound III with the yield of 90.1%. 300 mL 1,4-dioxane was added in a 500 mL eggplant-shaped flask, the compound III (20.00 g, 82.07 mmol), a compound 4-fluoro-2-methoxy-5-nitroaniline (16.80 g, 90.28 mmol) and p-toluenesulfonic acid (17.17 g, 90.28 mmol) were added into the eggplant-shaped flask respectively. The temperature rises to 85° C. for reaction for 8 h, the mixture was cooled to room temperature, was added with water for stirring, was dropwise added with 40% sodium hydroxide solution until the pH equals to 9, and was filtered, solid was washed with ethanol and dried under vacuum to obtain 30.00 g of yellow solid which is the compound 8 with the yield of 92.9%.

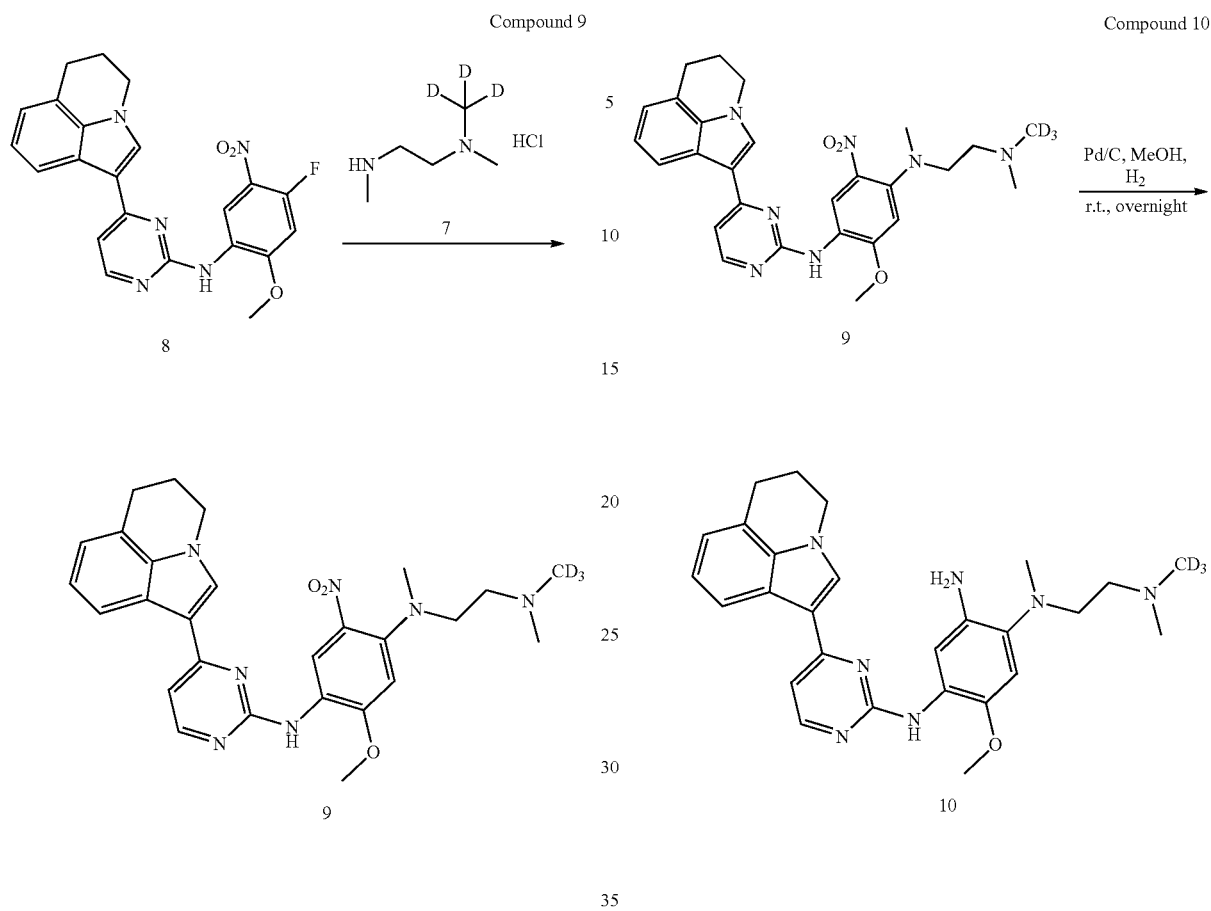

A 120 mL sealed tube was taken, and the compound 8 (2 g, 4.77 mmol), the compound 7 (810 mg, 5.72 mmol), DIPEA (1.23 g, 9.54 mmol) and DMA (10 mL) were added into the sealed tube. The mixture was reacted in the sealed tube at the temperature of 140° C. for 6 h, no raw material remaining was monitored by TLC, a reaction solution was cooled to room temperature, was added with 20 mL of water, and was separated out to obtain solid, the solid was filtered, a filter cake was added into 2 mL of methanol for pulping and washing, and filtering and drying were carried out to obtain 1.7 g of red solid which is the compound 9 with the yield of 70.6%.

A 250 mL single-neck flask was taken, the compound 9 (1.7 g, 3.37 mmol), Pd/C (200 mg) and MeOH (100 mL) were added into the single-neck flask, hydrogen is changed for 3 times by vacuum pumping, the mixture was stirred overnight at room temperature, no raw material remaining was monitored by TLC, Pd/C was removed by filtration, a solvent was distilled off under reduced pressure to obtain yellow green solid, and the solid was purified by column chromatography, and was eluted by an eluent (DCM:MeOH:$NH_3H_2O$=20:1:0.1) to obtain 1.2 g of yellow green solid which is the compound 10 with the yield of 75%.

Compound Shown in Formula I

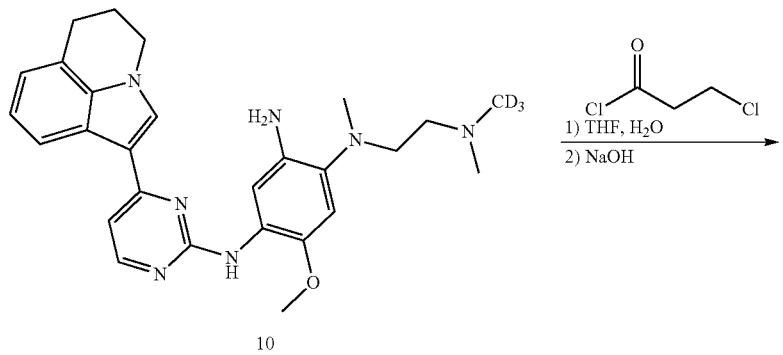

-continued

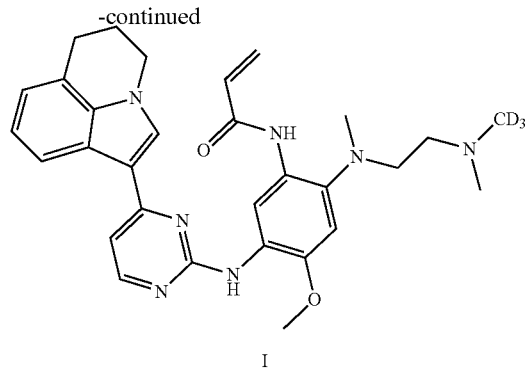

I

A 20 mL single-neck flask was taken, the compound 10 (500 mg, 1.05 mmol) and DCM (30 mL) were added into the single-neck flask, then 3-chloropropionyl chloride (133.7 mg, 1.05 mmol) was slowly dropwise added into a reaction solution at 0° C., the reaction solution was kept stirring for 30 min at room temperature, no raw material remaining was monitored by TLC, then NaOH (168 mg, 4.2 mmol) was added into the reaction solution, the reaction solution was heated to 65° C. and was stirred overnight, no raw material remaining was monitored by HPLC, a solvent was distilled off under reduced pressure, and the mixture was purified by column chromatography and was eluted by eluent (DCM: MeOH=10:1) to obtain 280 mg of faint yellow solid which is the compound shown in formula I, and the yield of the compound was 50.4%.

$^1$H NMR (400 MHz, CDCl3) δ 10.19 (s, 1H), 9.88 (s, 1H), 9.12 (s, 1H), 8.39 (d, J=5.3 Hz, 1H), 7.85 (d, J=8.0 Hz, 1H), 7.74 (s, 1H), 7.26-7.14 (m, 2H), 7.00 (d, J=7.0 Hz, 1H), 6.82 (s, 1H), 6.49 (dd, J=16.9, 2.2 Hz, 1H), 6.39 (dd, J=16.9, 9.8 Hz, 1H), 5.73 (dd, J=9.8, 2.2 Hz, 1H), 4.49-4.32 (m, 2H), 3.91 (s, 3H), 3.05 (t, J=6.0 Hz, 2H), 2.95-2.87 (m, 2H), 2.73 (s, 3H), 2.39-2.23 (m, 7H), 1.82 (s, 3H). LC-MS [M+H]$^+$ 528.7

Embodiment 2: Preparation of a Crystal Form A of Monomethanesulfonate of a Compound Shown in Formula I 1.0 g of the compound shown in formula I was added into 15 ml of dichloromethane, the mixture was stirred until the solution is clear, prepared methanesulfonic acid (182 mg of methanesulfonic acid may be dissolved into 5 ml of dichloromethane) was dropwise added at the controlled temperature of 30-50° C., the mixture was cooled to 0-30° C. for stirring and crystallization, was filtered and was dried under vacuum at 50° C. to obtain 1.1 g of the product with the yield of 93.0%, and the X-ray powder diffraction pattern, the infrared spectrogram, the thermogravimetric analysis graph (TG) and the differential scanning calorimetry curve graph (DSC) are respectively shown in FIG. 1, FIG. 2, FIG. 3 and FIG. 4.

Embodiment 3: Preparation of the Crystal Form A of the Monomethanesulfonate of the Compound Shown in Formula I 0.5 g of the compound shown in formula I was added into 10 ml of dichloromethane, the mixture was stirred until the solution is clear, prepared methanesulfonic acid (90 mg of methanesulfonic acid may be dissolved into 2.5 ml of dichloromethane) was dropwise added at the controlled temperature of 30-50° C., the mixture was cooled to 0-30° C. for stirring and crystallization, was filtered and was dried under vacuum at 50° C. to obtain 500 mg of the product with the yield of 84.7%, and the X-ray powder diffraction pattern and the infrared spectrogram were within an error range compared to embodiment 2.

Embodiment 4: Preparation of a Crystal Form B of the Monomethanesulfonate of the Compound Shown in Formula I 20 g of the compound shown in formula I was added into 400 ml of acetone, the mixture was heated until refluxing, methanesulfonic acid (3.6 g of methanesulfonic acid) was dropwise added, the mixture was cooled to 0-30° C., was stirred and crystallized for 4 h at controlled temperature, was filtered, and was dried under vacuum at 50° C. to obtain 21.6 g of the product with the yield of 91.5%. The X-ray powder diffraction pattern, the infrared spectrogram, the thermogravimetric analysis graph (TG) and the differential scanning calorimetrycurve graph (DSC) are respectively shown in FIG. 5, FIG. 6, FIG. 7 and FIG. 8.

Example 5: Preparation of the Crystal Form B of the Monomethanesulfonate of the Compound Shown in Formula I 500 g of the compound shown in formula I was added into 10 L of acetone, the mixture was heated until refluxing, methanesulfonic acid (90.9 g of methanesulfonic acid) was dropwise added, the mixture was cooled to 0-30° C., was stirred and crystallized for 4 h at controlled temperature, was filtered, and was dried under vacuum at 50° C. to obtain 550 g of the product with the yield of 93.0%, and the X-ray powder diffraction pattern and the infrared spectrogram were within an error range compared to embodiment 4.

Example 6: Preparation of the Crystal Form B of the Monomethanesulfonate of the Compound Shown in Formula I 30 g of the compound shown in formula I was added into 300 ml of acetonitrile, the mixture was heated until refluxing, methanesulfonic acid (5.5 g of methanesulfonic acid) was dropwise added, the mixture was cooled to 0-30° C., was stirred and crystallized for 4 h at controlled temperature, was filtered, and was dried under vacuum at 50° C. to obtain 31 g of the product with the yield of 87.3%, and the X-ray powder diffraction pattern and the infrared spectrogram were within an error range compared to embodiment 4.

Effect Embodiment: Properties of the Crystal Forms A and B of the Monomethanesulfonate of the Compound Shown in Formula I 1. Stability Differential Scanning Calorimetry (DSC) Test
Instrument: NETZSCH DSC 204 type differential thermal analyzer
Rate of temperature rise: 10.00° C./min The result shows that the crystal forms A and B of the monomethanesulfonate of the compound shown in formula I have DSC graphs basically shown in FIG. 8 and FIG. 4 respectively, and a single peak value is observed, proving that the crystal forms have stable heat exchange range.

2. Crystal Influence Factor Test

Samples of the crystal forms A and B of the monomethanesulfonate of the compound shown in formula I were exposed to high-temperature, high-humidity and illumination conditions for 15 days respectively, and the results showed that the crystal form A of the monomethanesulfonate was converted to the crystal form B of the monomethanesulfonate at high temperature and high humidity.

3. Accelerated Lofting Test

A sample of the crystal form B of the monomethanesulfonate of the compound shown in formula I was placed in a petri dish and was sampled and tested at 0 hour, 1 month, 2 months, 3 months, and 6 months respectively at a temperature of 40±2° C. and a relative humidity of 75%±5%, with the results shown in Table 1:

TABLE 1

Accelerated Lofting Test of the Crystal Form B of Monomethanesulfonate of the Compound Shown in Formula I

| Investigation items | Standard limit | Time (month) | | | | |
|---|---|---|---|---|---|---|
| | | 0 | 1 | 2 | 3 | 6 |
| Appearance | White to faint yellow powder | Light yellow powder | Light yellow powder | Light yellow powder | Light yellow powder | Light yellow powder |
| Maximum individual impurity | ≤2.50 | 1.62 | 1.87 | 1.42 | 1.62 | 1.61 |
| Total impurity | ≤4.0% | 2.55 | 3.12 | 2.72 | 2.72 | 2.74 |
| Loss on drying | ≤1.0 | 0.08 | 0.03 | 0.03 | 0.03 | 0.14 |
| Methanesulfonic acid (%) | ≤15.0-15.8% | 15.5 | 15.2 | 15.4 | 15.4 | 15.4 |
| Content (%) | Should not be less than 78.0% | 80.5 | 82.2 | 82.3 | 79.5 | 80.8 |

Figure 9:
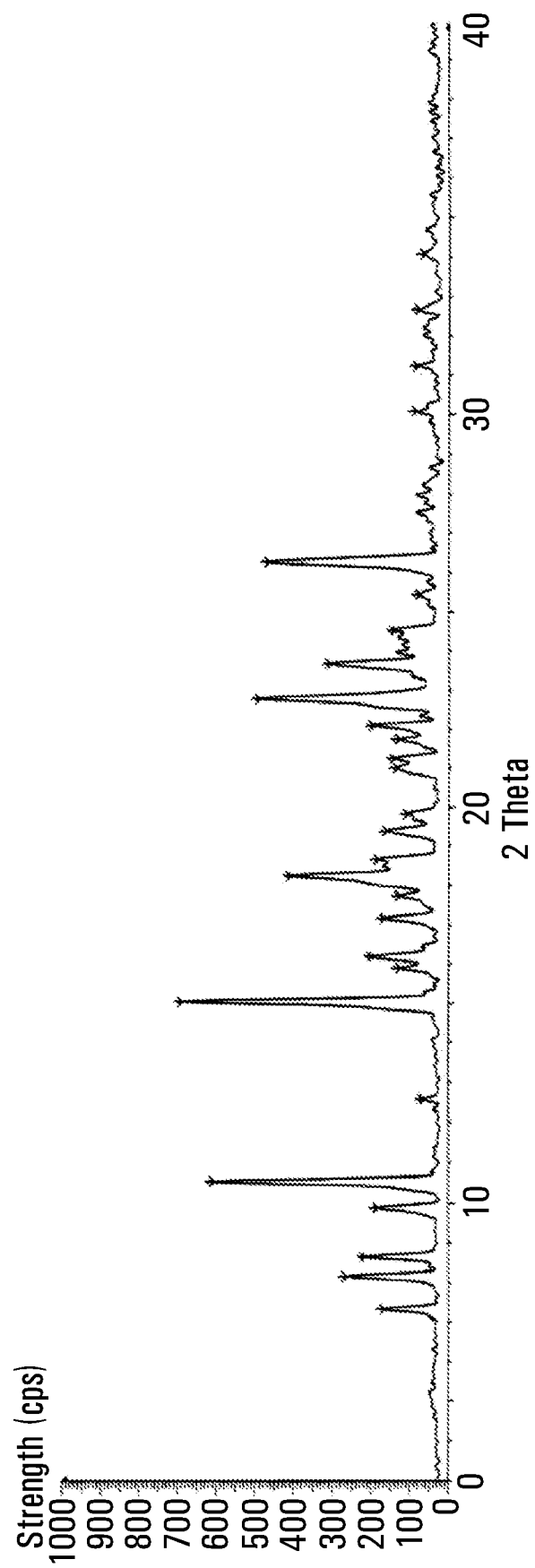
FIG. 9 is an X-ray powder diffraction pattern of the crystal form B of the monomethanesulfonate of the compound shown in formula I in the embodiment 4 in an accelerated lofting test for 6 months.

The above experiments proved that in the accelerated lofting experiment of the crystal form B of the monomethanesulfonate of the compound shown in formula I, all investigation items have no obvious change; and meanwhile, the X-ray powder diffraction pattern (FIG. 9) of the sample of the crystal form B of the monomethanesulfonate of the compound shown in formula I in the accelerated lofting test for 6 months is compared with the pattern (FIG. 1) before the experiments, the change was within an error range, and the crystal form was not changed.

4. Long-Term Lofting Experiments

A sample of the crystal form B of the monomethanesulfonate of the compound shown in formula I was placed in a petri dish under the conditions of the temperature being 25±5° C. and the relative humidity being 60%±10% and was sampled and tested at 0 hour, 3 months, and 6 months respectively, with the results shown in Table 2:

TABLE 2

Long-term Lofting Experiments of the Crystal Form B of Monomethanesulfonate of the Compound Shown in Formula I

| Investigation items | Standard limit | Time (month) | | |
|---|---|---|---|---|
| | | 0 | 3 | 6 |
| Appearance | White to faint yellow powder | Yellow powder | Yellow powder | Yellow powder |
| Maximum individual impurity | ≤2.50 | 1.62 | 1.65 | 1.48 |
| Total impurity | ≤4.0% | 2.55 | 2.78 | 2.50 |
| Loss on diying | ≤1.0 | 0.08 | 0.08 | 0.6 |
| Methanesulfonic acid (%) | ≤15.0-15.8% | 15.5 | 15.4 | 15.4 |
| Content (%) | Should not be less than 78.0% | 80.5 | 80.0 | 82.3 |

Figure 10:
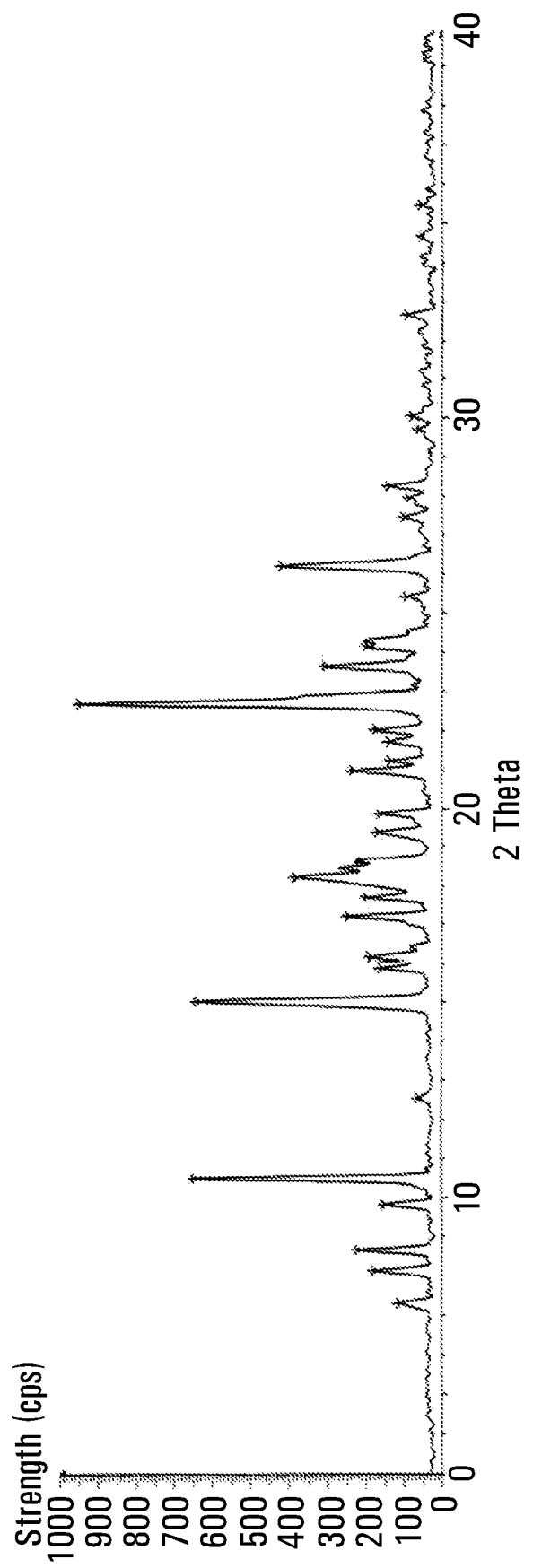
FIG. 10 is an X-ray powder diffraction pattern of the crystal form B of the monomethanesulfonate of the compound shown in formula I in the embodiment 4 in a long-term lofting test for 6 months.

The above experiments proved that in the long-term lofting experiment of the crystal form B of the monomethanesulfonate of the compound shown in formula I, all investigation items have no obvious change; and meanwhile, the X-ray powder diffraction pattern (FIG. 10) of the sample of the crystal form B of the monomethanesulfonate of the compound shown in formula I in the long-term lofting test for 6 months is compared with the pattern (FIG. 1) before the experiments, the change was within an error range, and the crystal form was not changed.

From the above results, it can be seen that in the accelerated lofting test (with the temperature of 40±2° C. and the relative humidity of 75%±5%) and the long-term lofting test (with the temperature of 25±5° C. and the relative humidity of 60%±10%), the crystal form, purity, and relative impurity of the crystal form B of the monomethanesulfonate of the compound shown in formula I involved in the present invention are not changed greatly, indicating the good stability of the crystal form B of the monomethanesulfonate of the compound shown in formula I.

What is claimed is:

1. 1. A crystal form A of monomethanesulfonate of a deuterated 3-(4,5-substituted aminopyrimidine)phenyl compound as represented by formula I:

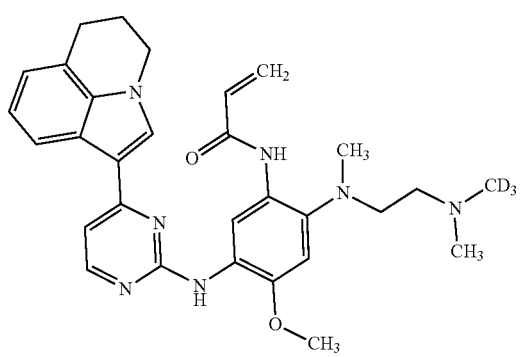

wherein in X-ray powder diffraction of the crystal form A, a 2θ diffraction angle has characteristic peaks at 15.42±0.2°, 17.86±0.2°, 20.58±0.2°, 21.58±0.2°, 23.86±0.2°, and 24.96±0.2°.

2. The crystal form A according to claim 1, wherein in the X-ray powder diffraction, the 2θ diffraction angle also has characteristic peaks at 6.34±0.2°, 10.24±0.2°, 10.72±0.2°, 14.94±0.2°, 15.42±0.2°, 16.88±0.2°, 17.86±0.2°, 20.58±0.2°, 21.58±0.2°, 23.86±0.2°, 24.96±0.2°, 26.28±0.2°, and 27.58±0.2°.

3. The crystal form A according to claim 1, having an X-ray powder diffraction pattern as shown in FIG. 1.

Figure 3:
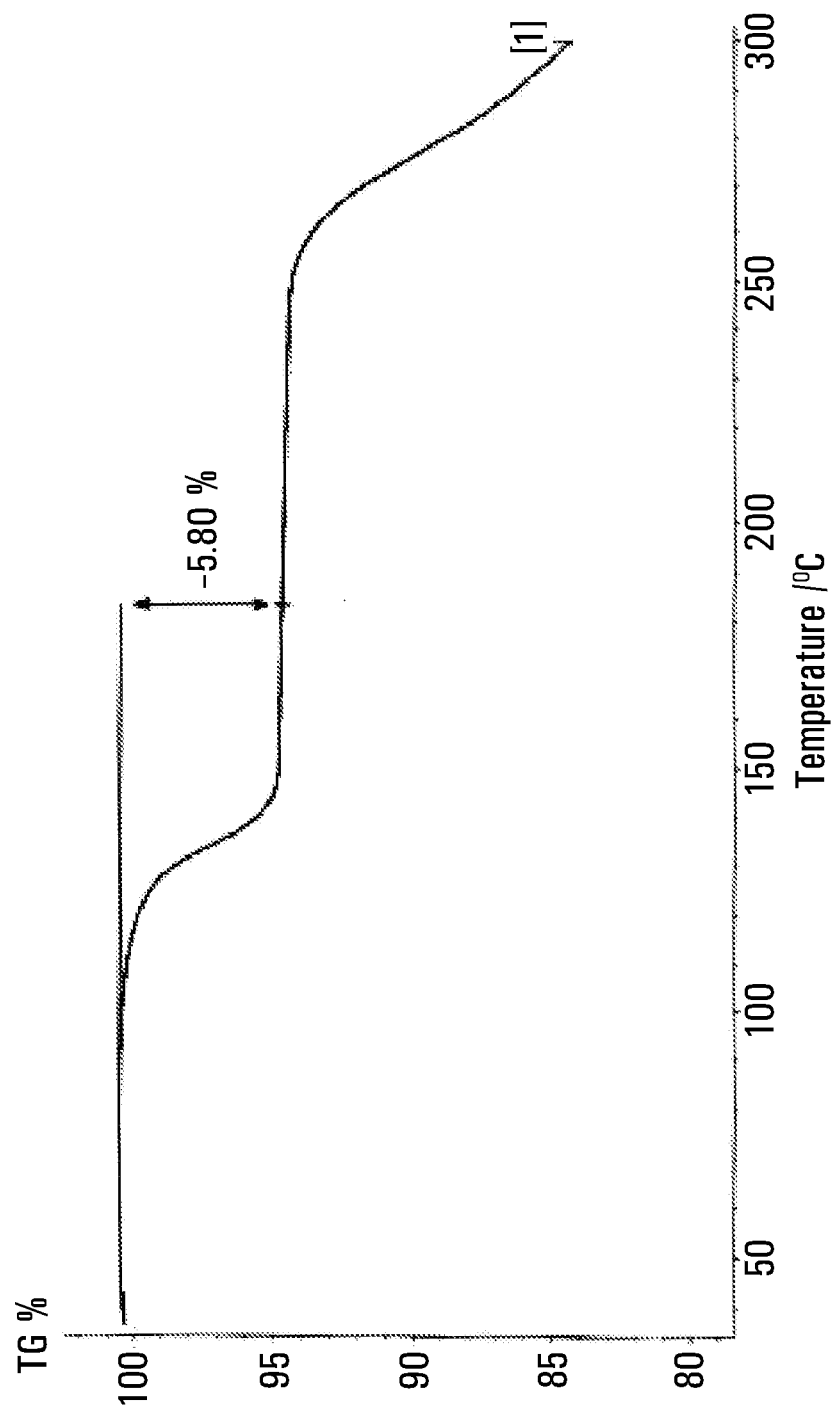
FIG. 3 is a thermogravimetric analysis graph (TG) of the crystal form A of the monomethanesulfonate of the compound shown in formula I in the embodiment 2.
Figure 4:
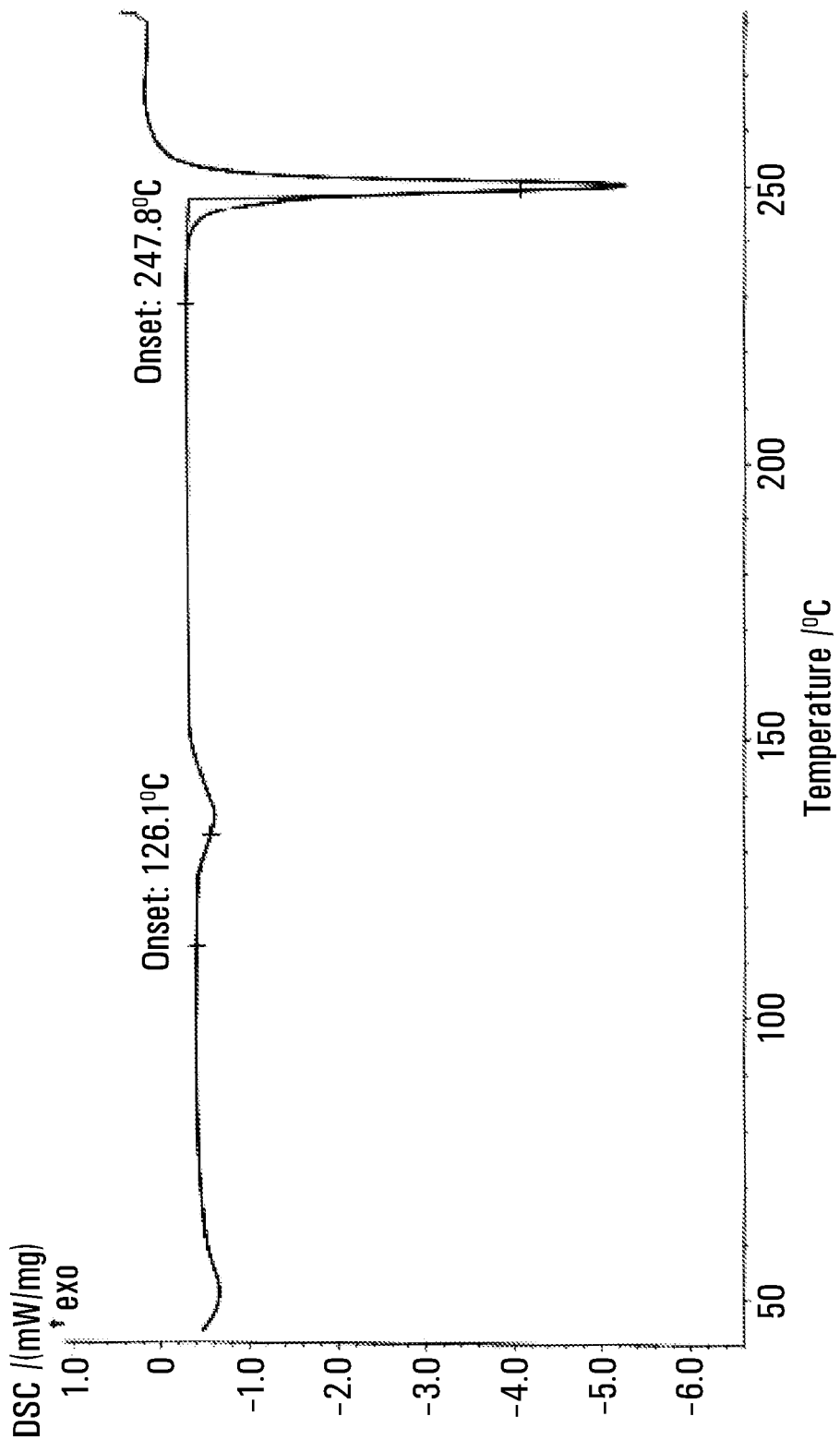
FIG. 4 is a differential scanning calorimetry curve graph (DSC) of the crystal form A of the monomethanesulfonate of the compound shown in formula I in the embodiment 2.

4. The crystal form A according to claim 1, having a thermogravimetric analysis graph as shown in FIG. 3 and a differential scanning calorimetry curve as shown in FIG. 4.

5. The crystal form A according to claim 1, having infrared spectra with the following characteristic absorption peaks: 3249 $cm^{-1}$, 3019 $cm^{-1}$, 1942 $cm^{-1}$, 1906 $cm^{-1}$, 1672 $cm^{-1}$, 1575 $cm^{-1}$, 1552 $cm^{-1}$, 1411 $cm^{-1}$, 1368 $cm^{-1}$, 727 $cm^{-1}$, 558 $^{-1}$, and 522 $cm^{-1}$.

6. A crystal form B of monomethanesulfonate of a deuterated 3-(4,5-substituted aminopyrimidine)phenyl compound as represented by formula I:

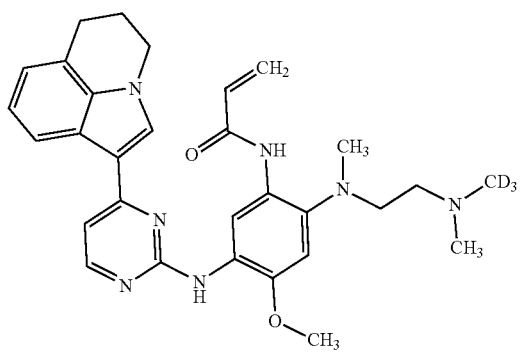

I wherein in X-ray powder diffraction of the crystal form B, a 2θ diffraction angle has characteristic peaks at 10.38±0.2°, 14.9±0.2°, 18.1±0.2°, 22.68±0.2°, and 26.20±0.2°.

7. The crystal form B according to claim 6, wherein in the X-ray powder diffraction of the crystal form B, the 2θ diffraction angle also has characteristic peaks at 7.20±0.2°, 8.00±0.2°, 8.50±0.2°, 10.38±0.2°, 14.9±0.2°, 16.06±0.2°, 18.1±0.2°, 19.28±0.2°, 20.88±0.2°, 21.96±0.2°, 22.68±0.2°, 23.54±0.2°, and 26.20±0.2°.

Figure 5:
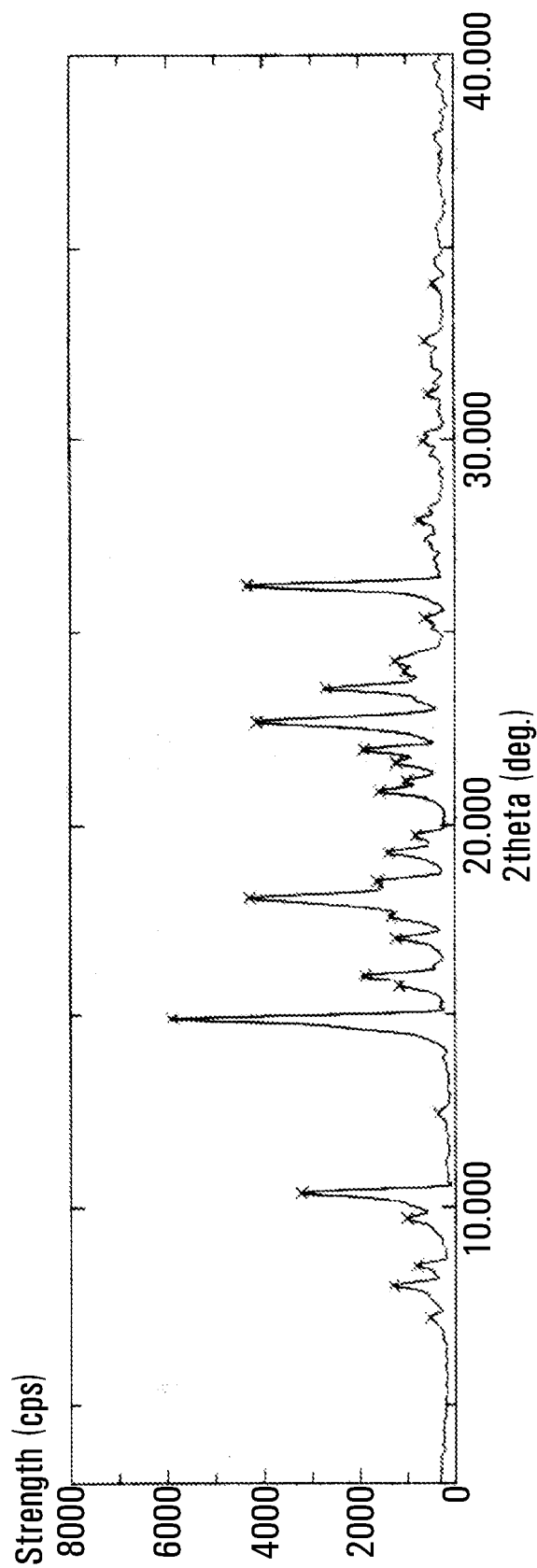
FIG. 5 is an X-ray powder diffraction pattern of a crystal form B of the monomethanesulfonate of the compound shown in formula I in an embodiment 4.
Figure 6:
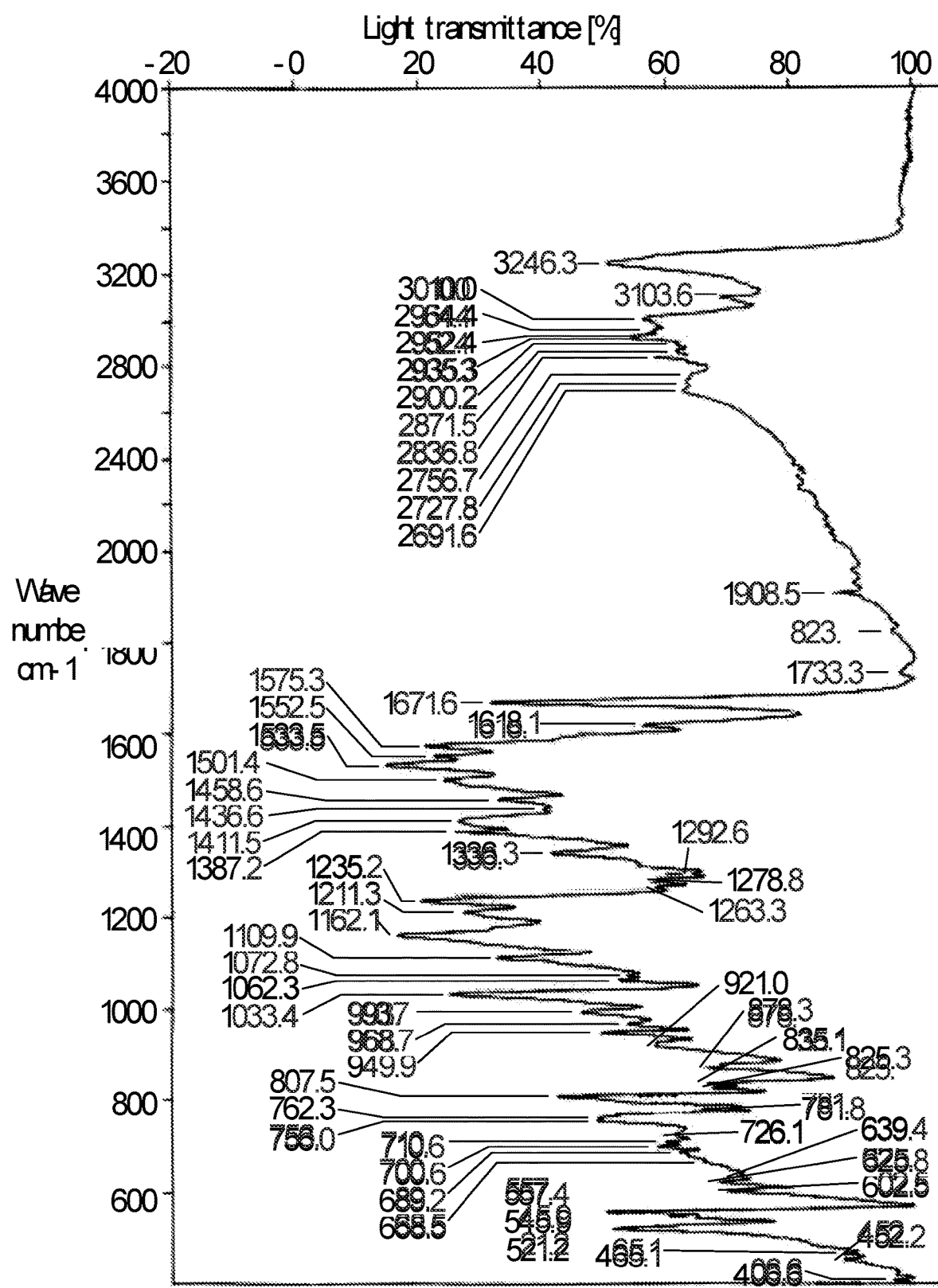
FIG. 6 is an infrared spectrogram of the crystal form B of the monomethanesulfonate of the compound shown in formula I in the embodiment 4.

8. The crystal form B according to claim 6, having an X-ray powder diffraction pattern as shown in FIG. 5.

Figure 7:
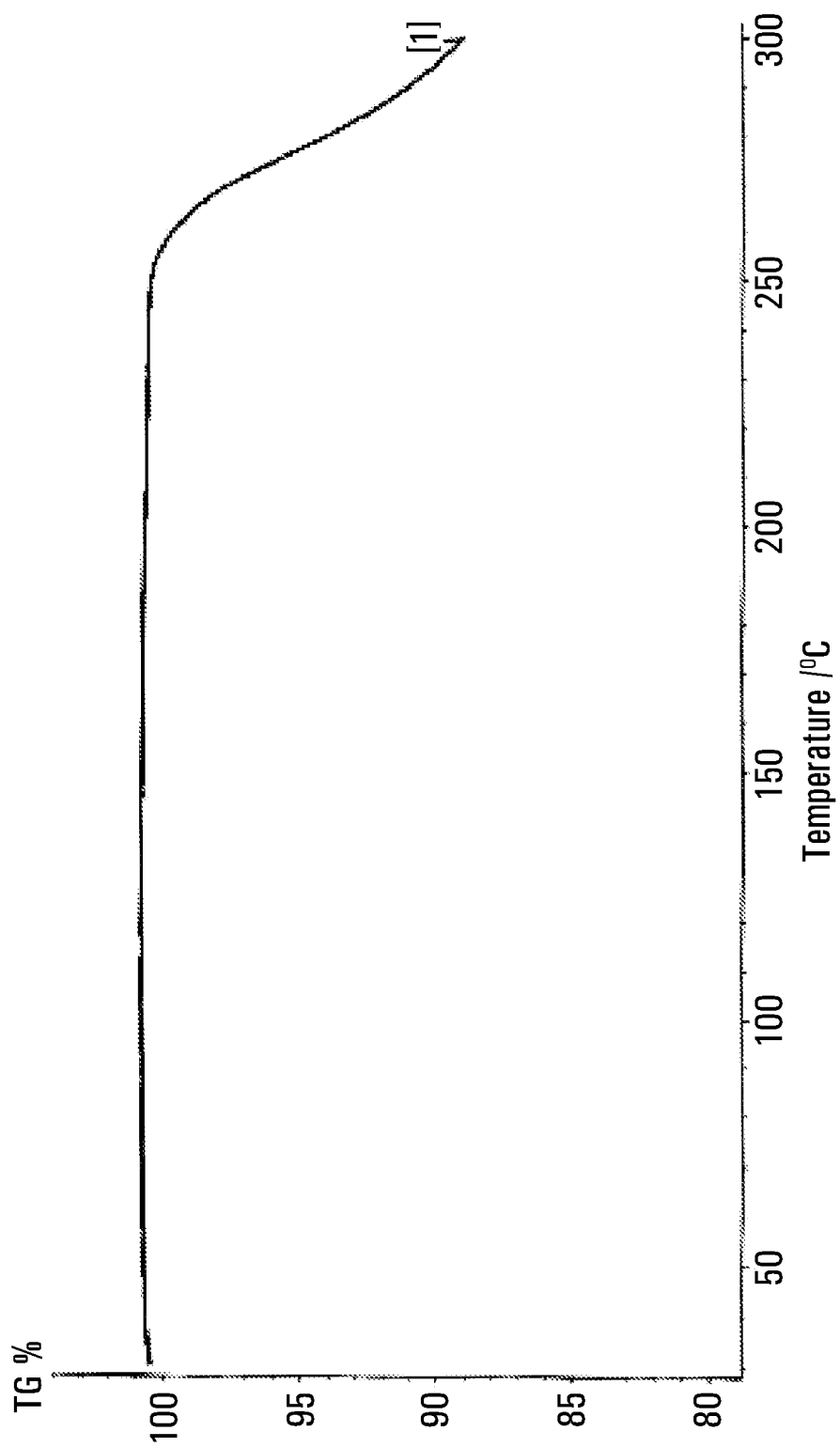
FIG. 7 is a thermogravimetric analysis graph (TG) of the crystal form B of the monomethanesulfonate of the compound shown in formula I in the embodiment 4.
Figure 8:
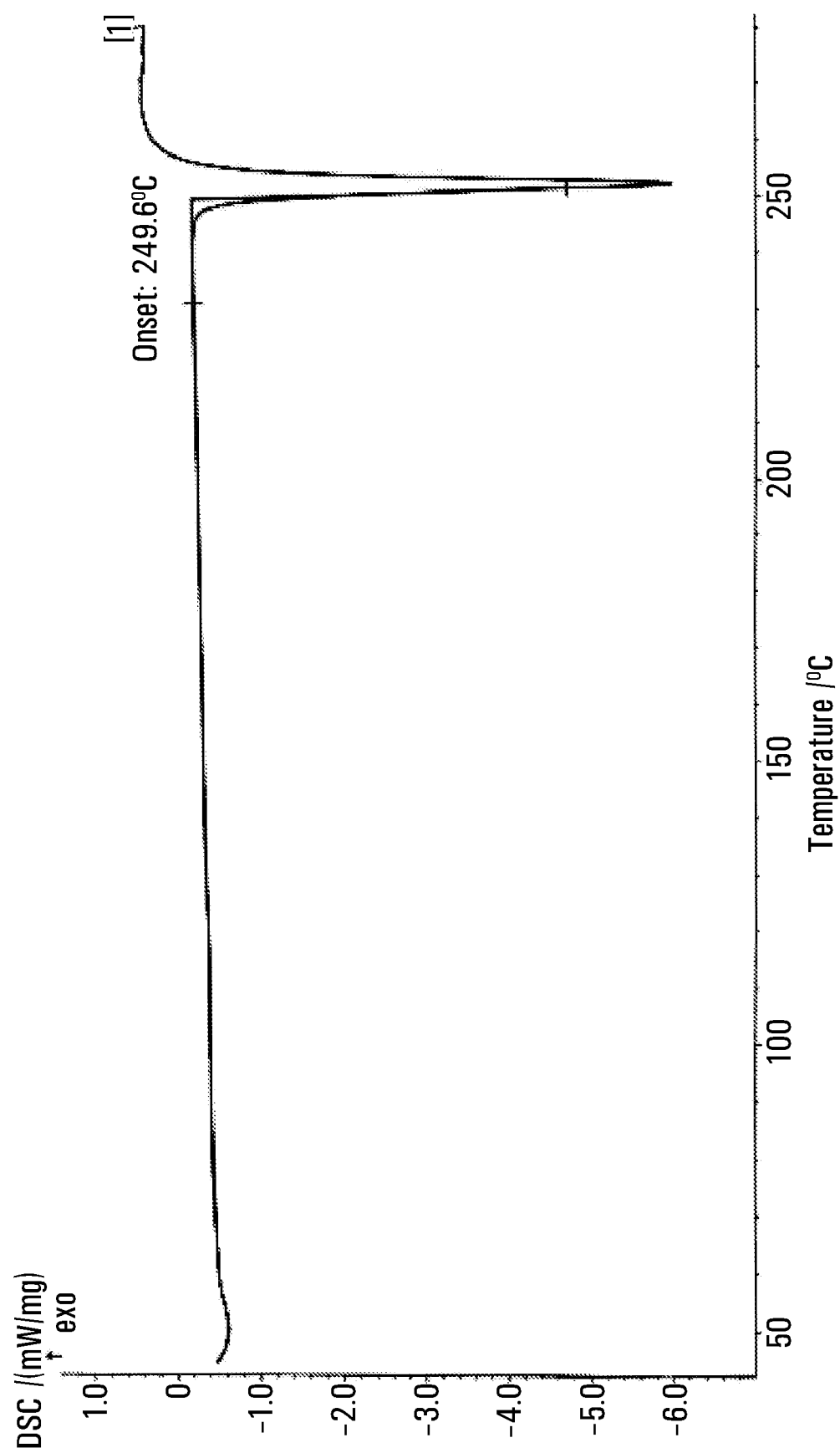
FIG. 8 is a differential scanning calorimetry curve graph (DSC) of the crystal form B of the monomethanesulfonate of the compound shown in formula I in the embodiment 4.

9. The crystal form B according to claim 6, having a thermogravimetric analysis graph as shown in FIG. 7 and a differential scanning calorimetry curve as shown in FIG. 8.

10. The crystal form B according to claim 6, having infrared spectra with the following characteristic absorption peaks: 3248 $cm^{-1}$, 3103 $cm^{-1}$, 1906 $cm^{-1}$, 1671 $cm^{-1}$, 1618 $cm^{-1}$, 1575 $cm^{-1}$, 1533 $cm^{-1}$, 1141 $cm^{-1}$, 1235 $cm^{-1}$, 1162 $cm^{-1}$, and 807 $cm^{-1}$.

11. A preparation method of the crystal form B according to claim 6, comprising following steps:
   1) mixing the deuterated 3-(4,5-substituted aminopyridine)phenyl compound of formula I with a solvent at the temperature of 50-80° C., and dropwise adding methanesulfonic acid;
   2) stirring and crystallizing at the temperature of 0-30° C.; and
   3) filtering and drying to obtain the crystal form B.

12. The preparation method according to claim 11, wherein the solvent in step 1) is selected from acetonitrile, acetone or a mixture of acetonitrile and acetone, and the use amount of the solvent is 5-40 times that of deuterated 3-(4,5-substituted aminopyridine)phenyl compound of formula I in mL/g units.

13. The preparation method according to claim 12, wherein the use amount of the solvent in step 1) is 10-20 times that of deuterated 3-(4,5-substituted aminopyridine) phenyl compound of formula I in mL/g units.

14. The preparation method according to claim 11, wherein the molar ratio of methanesulfonic acid to deuterated 3-(4,5-substituted aminopyridine)phenyl compound of formula I in step 1) is (0.1-1):1.

15. A pharmaceutical composition comprising crystal form A according to claim 1 and a pharmaceutically acceptable carrier.

16. A method of treating a human or an animal afflicted with a tumor comprising administering an effective amount of the pharmaceutical composition of claim 15 to the human or animal so as to treat the human or animal.

17. A pharmaceutical composition comprising crystal form B according to claim 6 and a pharmaceutically acceptable carrier.

18. A method of treating a human or an animal afflicted with a tumor comprising administering an effective amount of the pharmaceutical composition of claim 17 to the human or animal so as to treat the human or animal.

* * * * *